(12) United States Patent
Hamel (10) Patent No.: US 7,766,825 B2
(45) Date of Patent: Aug. 3, 2010

(54) RETRACTOR WITH INTERCHANGEABLE RETRACTOR BLADES

(75) Inventor: Ross J. Hamel, West Chester, PA (US)

(73) Assignee: Synthes USA, LLC, West Chester, PA (US)

( * ) Notice: Subject to any disclaimer, the term of this patent is extended or adjusted under 35 U.S.C. 154(b) by 314 days.

(21) Appl. No.: 10/676,170

(22) Filed: Oct. 2, 2003

(65) Prior Publication Data

US 2004/0147812 A1  Jul. 29, 2004

Related U.S. Application Data

(60) Provisional application No. 60/415,135, filed on Oct. 2, 2002.

(51) Int. Cl.
*A61B 1/32* (2006.01)
(52) U.S. Cl. .................. 600/213; 600/226; 600/227
(58) Field of Classification Search ............... 600/201, 600/234, 210–213, 217, 221–228, 205; 403/43, 403/44, 118, 45, 109.4
See application file for complete search history.

(56) References Cited

U.S. PATENT DOCUMENTS

| | | | | | |
|---|---|---|---|---|---|
| 3,965,890 | A | * | 6/1976 | Gauthier | 600/215 |
| 4,116,232 | A | | 9/1978 | Rabban | |
| 4,232,660 | A | | 11/1980 | Coles | 128/20 |
| 4,562,832 | A | * | 1/1986 | Wilder et al. | 600/223 |
| 4,608,972 | A | | 9/1986 | Small | 128/92 EB |
| 4,616,634 | A | | 10/1986 | Vargas Garcia | 128/20 |
| 4,619,248 | A | * | 10/1986 | Walsh | 600/223 |
| 4,683,896 | A | | 8/1987 | Herbst et al. | 128/785 |
| 4,713,077 | A | | 12/1987 | Small | 623/16 |
| 4,769,011 | A | * | 9/1988 | Swaniger | 604/218 |
| 4,905,670 | A | * | 3/1990 | Adair | 600/104 |
| 4,934,352 | A | | 6/1990 | Sullivan, Jr. | 128/20 |
| 5,026,376 | A | | 6/1991 | Greenberg | 606/96 |
| 5,035,232 | A | | 7/1991 | Lutze et al. | 128/20 |
| 5,133,720 | A | | 7/1992 | Greenberg | 606/96 |
| 5,143,054 | A | * | 9/1992 | Adair | 600/104 |
| 5,147,367 | A | | 9/1992 | Ellis | 606/96 |
| 5,190,549 | A | | 3/1993 | Miller et al. | 606/85 |
| 5,251,613 | A | * | 10/1993 | Adair | 600/109 |
| 5,407,427 | A | * | 4/1995 | Zhu et al. | 604/26 |
| 5,558,622 | A | * | 9/1996 | Greenberg | 600/237 |
| 5,688,223 | A | * | 11/1997 | Rosendahl | 600/215 |
| 5,746,743 | A | * | 5/1998 | Greenberg | 606/96 |

(Continued)

FOREIGN PATENT DOCUMENTS

GB    2 133 694    8/1984

(Continued)

*Primary Examiner*—Cris L Rodriguez
*Assistant Examiner*—Hao D Mai
(74) *Attorney, Agent, or Firm*—Woodcock Washburn LLP (57) ABSTRACT

The present invention relates to a surgical retractor. The surgical retractor may include a handle having a longitudinal axis and proximal and distal ends, a first coupling mechanism adjacent the proximal end of the handle, and a blade member having a proximal end and a distal end. The blade member may have a coupling element, and the coupling element may be configured and dimensioned to connect with the first coupling mechanism. The present invention also relates to methods for treating bone.

28 Claims, 4 Drawing Sheets

U.S. PATENT DOCUMENTS

| | | | |
|---|---|---|---|
| 5,755,721 A | 5/1998 | Hearn | 606/96 |
| 5,817,005 A * | 10/1998 | Cohen | 600/201 |
| 5,846,187 A | 12/1998 | Furnish et al. | |
| 5,846,249 A * | 12/1998 | Thompson | 606/119 |
| 5,882,298 A * | 3/1999 | Sharratt | 600/213 |
| 5,902,233 A * | 5/1999 | Farley et al. | 600/213 |
| 5,902,315 A | 5/1999 | DuBois | 606/190 |
| 5,904,650 A * | 5/1999 | Wells | 600/226 |
| 5,921,919 A | 7/1999 | Chin et al. | 600/217 |
| 5,922,004 A | 7/1999 | DuBois | 606/190 |
| 5,938,592 A * | 8/1999 | Koteles et al. | 600/228 |
| 5,944,736 A * | 8/1999 | Taylor et al. | 606/198 |
| 5,957,927 A | 9/1999 | Magee et al. | 606/99 |
| 5,984,865 A * | 11/1999 | Farley et al. | 600/213 |
| 6,033,361 A | 3/2000 | Co et al. | 600/210 |
| 6,042,540 A | 3/2000 | Bass et al. | |
| 6,053,863 A | 4/2000 | Chin et al. | 600/217 |
| 6,080,105 A | 6/2000 | Spears | 600/212 |
| 6,083,153 A * | 7/2000 | Rullo et al. | 600/217 |
| 6,090,042 A * | 7/2000 | Rullo et al. | 600/210 |
| 6,132,370 A | 10/2000 | Furnish et al. | |
| 6,139,493 A | 10/2000 | Koros et al. | 600/215 |
| 6,228,025 B1 * | 5/2001 | Hipps et al. | 600/213 |
| 6,254,535 B1 * | 7/2001 | Furnish et al. | 600/213 |
| 6,350,236 B1 * | 2/2002 | Hipps et al. | 600/213 |
| 6,354,994 B1 * | 3/2002 | Rullo et al. | 600/217 |
| 6,371,968 B1 * | 4/2002 | Kogasaka et al. | 606/190 |
| 6,442,781 B1 | 9/2002 | Chen | |
| 6,524,238 B2 | 2/2003 | Velikaris et al. | 600/213 |
| 6,572,540 B2 * | 6/2003 | Dobrovolny | 600/226 |
| 2002/0035313 A1* | 3/2002 | Scirica et al. | 600/233 |
| 2002/0077530 A1 | 6/2002 | Velikaris et al. | 600/213 |
| 2002/0138079 A1 | 9/2002 | Cohen | |

FOREIGN PATENT DOCUMENTS

| | | |
|---|---|---|
| WO | WO 02/19919 A2 | 3/2002 |

\* cited by examiner

RETRACTOR WITH INTERCHANGEABLE RETRACTOR BLADES

CROSS-REFERENCE TO RELATED APPLICATIONS

This application claims the benefit under 35 U.S.C. §119(e) of U.S. Provisional Application No. 60/415,135, filed Oct. 2, 2002, the entire contents of which are expressly incorporated herein by reference thereto.

FIELD OF THE INVENTION

This invention relates to medical instruments and, more particularly, to surgical retractors. The invention also relates to surgical procedures and, more particularly, to surgical procedures for treating bone.

BACKGROUND OF THE INVENTION

During a surgical procedure, it may be appropriate to prevent trauma to the patient and to attempt to reduce damage to tissue surrounding a surgical site. Surgeons, therefore, may make appropriately sized incisions when performing a surgical procedure. A surgeon performing surgery may further prefer a clear and/or stabilized view of the operating field. Retractors may be used during surgery to open an incision and provide a view of the field of the operation.

SUMMARY OF THE INVENTION

The present invention relates to a surgical retractor having, in an exemplary embodiment, a primary handle having a distal end and a proximal end. The surgical retractor may also have a first coupling mechanism located at the proximal end of the primary handle, and in addition may also have a second coupling mechanism located at the proximal end of the primary handle. Located at the distal end of the primary handle, in an exemplary embodiment, may be auxiliary handle. The auxiliary handle may provide an additional surface for gripping the retractor. The distal end of the primary handle may further include a bore having a threaded portion which may be configured to couple the auxiliary and primary handles.

In one development, the first coupling mechanism may be designed to secure interchangeable retractor blades to the handle, and the second coupling mechanism may be designed to secure a secondary surgical instrument, such as a light pipe or endoscope-type instrument, to the primary handle at a user desired orientation.

In an exemplary embodiment, the first coupling mechanism may be comprised of a rotatable knob disposed within the handle. The knob may have a bore which extends axially from approximately the center of the knob to an upper surface of the knob. The bore, may be threaded and designed to receive a connector located on the bottom of a retractor blade. In another development, a shoulder may be located on the upper surface of the primary handle to aid in coupling the retractor blade to the primary handle. The shoulder located on the upper surface of the primary handle may abut the back end of the retractor blade and prevent the retractor blade from rotating with respect to the handle, once the blade is coupled to the handle. In an illustrative embodiment, the shoulder may have a protrusion for engaging a notch that may be present at the back end of the retractor blade.

In another development, the second coupling mechanism may include a knob, an inner sleeve, and a clamping member. The knob may have a bore which extends axially from approximately the center of the knob to an upper surface of the knob. An inner sleeve may surround a portion of the clamping member. An upper surface of the inner sleeve may be configured and dimensioned to operatively interface with the clamping member. In an illustrative embodiment, the clamping member may have, near its lower surface, a shaft that may be designed to engage the bore in the knob. The clamping member may have a through-hole near its upper surface for receiving a secondary surgical instrument. In an exemplary embodiment, the knob, the through-hole located in the clamping member, and the upper surface of the inner sleeve operatively interface to clamp the secondary surgical instrument in place.

In another development, the retractor blade may be substantially straight along its longitudinal length from the distal end to near the proximal end. The blade may include a transverse concavity. In an illustrative embodiment, the proximal end of the retractor blade may include a notch for engagement with the protrusion located on the retractor handle shoulder. Located adjacent the proximal end of the blade, may be a connector that extends downwardly from the blade. The distal end of the retractor blade may be straight. Alternatively, the distal end of the blade may have a first curved portion. Also, at the end of the first curved portion, near the tip of the distal end of the blade, may be a second curved portion which has a generally hook-like shape. In another illustrative embodiment, the blade may be straight near the distal end. In another illustrative embodiment, located near the distal end of the blade may be an aperture extending from the upper surface of the blade to the lower surface of the blade.

In another exemplary embodiment, the surgical retractor may include a handle having a longitudinal axis and proximal and distal ends, a first coupling mechanism adjacent the proximal end of the handle, and a blade member having a proximal end and a distal end. The blade member may further have a coupling element, and the coupling element may be configured and dimensioned to connect with the first coupling mechanism.

In another development, the first coupling mechanism may have a knob having a bore. The bore may be transverse to the longitudinal axis of the handle. In an illustrative embodiment, the knob may be coupled to the handle by a pin. For instance, the pin may contact the bore, the bore may form an axial bore, and the pin may form an axle for the knob so the knob may rotate about the axle. In an illustrative embodiment, the bore may also extend from a first outer surface to a second outer surface of the knob. The bore may be further adapted to engage the coupling element of the blade member. For example, and without limitation, the coupling element may have a shaft. In one such embodiment, the shaft and the bore may have mating threads for releasably advancing the shaft within the bore. In an another development it may also be possible that the handle may have an opening that is configured and dimensioned to receive the knob.

In another development, the handle may have a surface for supporting the blade member. In an illustrative embodiment, the surface may have a curved portion. For example, and without limitation, the curved portion may be concave. In another example, the surface may have a contour that is configured and dimensioned to generally correspond with a portion of the blade member. In another development, the blade member may have a contour that is configured and dimensioned to generally correspond with a portion of the handle. For example, the blade member may have a longitudinal axis and a contour that defines a transverse concavity along the longitudinal axis of the blade member.

In another development, the blade member may also have an aperture near the distal end of the blade. In an illustrative embodiment, the aperture may be configured and dimensioned to allow a surgical tool to pass through the aperture. Examples of such a tool include but are not limited to a trochar, a cannula, an implant diver (such as a screw driver), a drill, and a syringe. In addition, the aperture may be configured and dimensioned to allow an orthopedic implant to pass through the aperture. Examples of such implants include, without limitation, a bone plate, a fastener (e.g., a screw, pin, nail, wire, or suture), or a bone void filler material (e.g., a bone cement, a bone cement substitute, a bone graft, or an allograft).

In another development, the distal end of the blade member may also have a structure for stabilizing the retractor blade against bone. For instance, the distal end of the blade member may have a hook-shape and/or projection. In one example, the structure includes a hook-shape that may generally form a "C"-shape. In another example, the structure includes a hook-shape that may generally from an "L"-shape.

In another development, the retractor may have a second coupling mechanism located on the handle for coupling a second surgical instrument to the handle. For instance, the second surgical instrument may be an endoscope or light source. An endoscope, for example, may be positioned to provide a view of the distal end of the retractor blade. The retractor may therefore include an endoscope or light source secured to the handle. In such an embodiment, the endoscope or light source may be positioned to view/light the distal end of the retractor blade.

In an exemplary embodiment, the second coupling mechanism may have a coupling member that may be located near the proximal end of the handle. The coupling member may be configured and dimension to be received within the handle. In an illustrative example, the coupling member may be telescopically received within the handle. The coupling member may or may not be spaced from the handle. The coupling member may contact a second member, for example, a sleeve. The second member may contact the handle. The coupling member and the second member may also be operatively associated to fixate a second surgical instrument with respect to the handle. For instance, a coupling member may be configured and dimensioned to translate, rotate, or translate and rotate with respect to a second member. In an illustrative embodiment, the coupling member may have a recess adapted to receive a portion of the second surgical instrument. The recess, for example, may have an inner surface, and the inner surface may be adapted to secure the portion of the second surgical instrument to the second member. In an exemplary embodiment, the inner surface of the recess may clamp the portion of the second surgical instrument to the second member.

In another development, the second coupling mechanism may have a protuberance, such as a knob, for controlling movement of the coupling member with respect to the handle. In an illustrative embodiment, the protuberance may be connected to the handle. For instance, the protuberance may include a structure (e.g., a flange, projection recess, groove, slot latch, rib, lock, or coupling) for securing the protuberance to the handle.

In another development, the protuberance may also have a structure (e.g., a flange, projection recess, groove, slot latch, rib, lock, or coupling) for securing the protuberance to the coupling member. In an illustrative embodiment, the protuberance may have a bore, and the bore may be configured and dimensioned to connect with the coupling member. The bore and the coupling member may also be operatively associated to provide controlled relative movement between the protuberance and the coupling member. For example, the bore and the coupling member may have mating threads.

In another development, the retractor may also include another surgical instrument having a coupling element configured and dimensioned to connect with the first coupling mechanism. In an illustrative embodiment, the other surgical instrument may include on or more retractor blades having similar or different shape. For instance, the retractor blades may have varying length, varying width, and/or varying degrees of concavity so that an operator may select a blade most suited for a clinical need.

In another development, the retractor may further include a second handle. In an illustrative embodiment, the second handle may be transverse to the longitudinal axis.

In yet another development, the retractor may be provided in a kit with other tools. For example, one retractor kit might include one or more primary handles, each handle having a proximal and distal end. The kit may further include one or more blade members each having a proximal end, a distal end, and a shaft portion proximate the proximal end of the blade. Each primary handle may have a first coupling mechanism located proximate the proximal end of the handle for coupling the blade to the handle. The coupling mechanism may be designed and configured to releasably couple with the shaft portion of the blade. The kit may also include one or more auxiliary handles. Each auxiliary handle may be designed and configured to couple proximate the distal end of at least one of the primary handles.

In use, the retractor may be used, for example, in surgical procedures for treating bone. For instance, the surgical retractor may be used by positioning an endoscope with respect to the retractor blade for viewing a surgical site that may be accessed in part by using the retractor to retract soft tissue from or near bone. In an illustrative example, an incision may be made in soft tissue and the soft tissue fascia may be elevated off a bone segment proximate the surgical site. The retractor blade may be passed through the incision. Fascia may be retracted off the bone segment with the retractor blade to form a cavity. A portion of the retractor blade may be placed in contact with—and/or may circumvent at least in part—a portion of the bone segment. The retractor blade may be stabilized on the bone segment. The bone segment may be viewed through the endoscope. A surgical procedure may be performed proximate the bone segment. The surgical procedure may also involve securing the endoscope with respect to the retractor blade.

In another development, the surgical procedure may involve passing an orthopedic implant through the cavity. Examples of such implants include, without limitation, a bone plate, a fastener (e.g., a screw, pin, nail, wire, or suture), or a bone void filler material (e.g., a bone cement, a bone cement substitute, a bone graft, or an allograft). In another development, a part of the surgical procedure may be performed through an aperture of the retractor blade. For instance, the surgical procedure may involve passing a surgical tool through an aperture of the retractor blade. Examples of surgical tools that may be passed through the aperture (in whole or in part) may include, without limitation, a drill, a burr, a syringe, and/or a cannula.

In another development, a surgical procedure may involve passing an orthopedic implant through the aperture. An suitable implant may be passed separate from or together with a surgical tool. Examples of such implants include, without limitation, a bone plate, a fastener (e.g., a screw, pin, nail, wire, or suture), or a bone void filler material (e.g., a bone cement, a bone cement substitute, a bone graft, or an allograft).

In yet another development, the surgical procedure may include securing an orthopedic implant to the bone segment. For instance, the surgical procedure may include fixating a fracture proximate the bone segment. In an illustrative example, the bone segment may be a condylar neck.

In yet another development, the surgical procedure may include performing an orthognathic procedure.

In yet another development, the surgical procedure may include a condylar grafting procedure. For instance, the grafting procedure may involve a bone segment of a ramus and/or a bone segment of the condylar neck and/or head.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein.

DETAILED DESCRIPTION OF THE PREFERRED EMBODIMENTS

Referring to the accompanying drawings, preferred embodiments and features of the surgical retractor will be described in detail. It is to be noted however that these descriptions of specific embodiments and features are merely illustrative. It is contemplated that one or more features or elements of the various embodiments may be combined or used singularly, and that modifications of the various embodiments, as well as other embodiments are contemplated and will be apparent to those persons skilled in the art.

Figure 1:
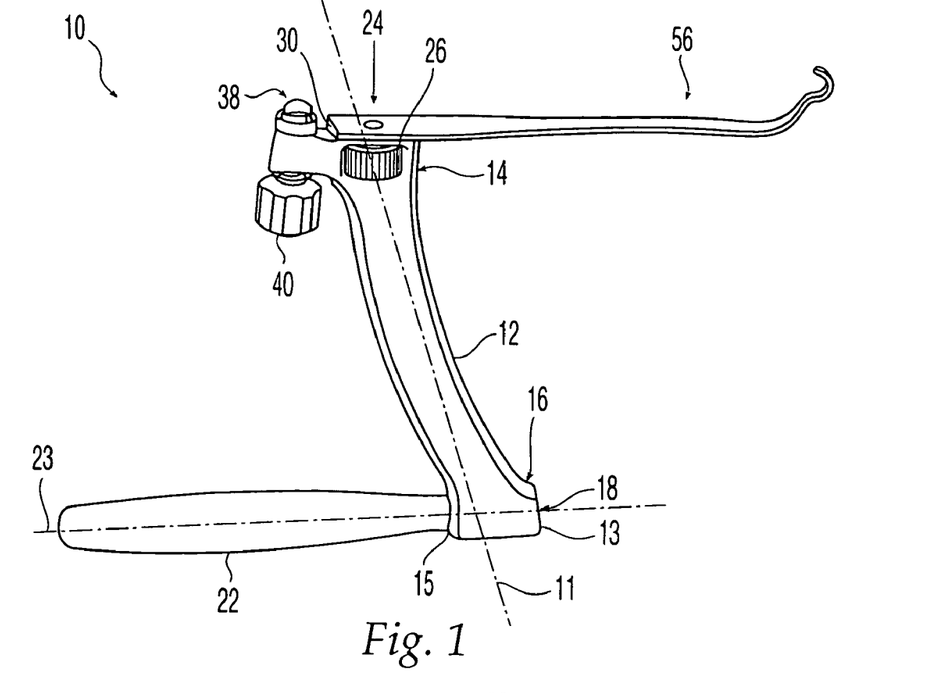
FIG. 1 is a perspective view of a first embodiment of a retractor according to the present invention.
Figure 2:
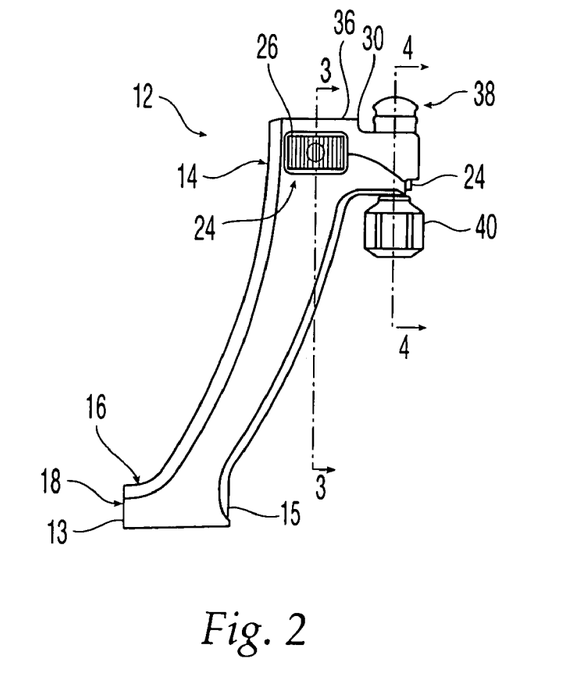
FIG. 2 is a side view of the handle of the retractor of FIG. 1.

Referring initially to FIG. 1, a perspective view of an exemplary first embodiment of a retractor 10 is shown. Retractor 10, preferably, has a primary handle 12 having a longitudinal axis 11, a proximal end 14 and a distal end 16. As shown in FIGS. 1 and 2, handle 12, preferably, is generally arcuate with a generally rectangular cross-sectional shape and is designed to comfortably interface with the operator's fingers and hands. Although handle 12 is shown as being arcuate with a generally rectangular cross-sectional shape, handle 12 may be any shape, preferably a shape that conforms ergonomically and comfortably with an operator's fingers and hands. For example, handle 12 may be rectangular, cylindrical, arcuate with a cylindrical shape, octagonal, arcuate with an octagonal shape, hexagonal, or arcuate with a hexagonal shape. Handle 12 may also be straight instead of the curved, arcuate shape as shown.

In an exemplary embodiment, distal end 16 of primary handle 12, handle 12 may include a bore 18 (not shown). Bore 18 preferably extends transverse to the longitudinal axis of handle 12 and may extend partially through handle 12, from front end 13 to generally the center of handle 12 or from back end 15 to generally the center of handle 12. In another exemplary embodiment, bore 18 may extend completely through handle 12, from front end 13 to back end 15. Bore 18 preferably includes threading for receiving a threaded shaft 20 (not shown) of an auxiliary handle 22. Depending on which side of handle 12 bore 18 is located, or if bore 18 is a through-bore, bore 18 will allow coupling of auxiliary handle 22 to handle 12 at either the front end 13 or the back end 15 of handle 12. Accordingly, depending on the holding surface required and/or the position of the operator, auxiliary handle 22 may be coupled to handle 12 extending in a direction as shown in FIG. 1, or auxiliary handle 22 may be coupled to handle 12 extending in a direction opposite to the direction shown in FIG. 1. It will be appreciated that auxiliary handle 22, in the embodiment, shown may be releasably coupled and uncoupled to handle 12, and further that auxiliary handle 22 maybe fixedly coupled to handle 12.

In addition, although auxiliary handle 22 is generally oriented so that longitudinal axis 23 is generally at an angle of about 93° to about 105° with respect to longitudinal axis 11 of handle 12, it can be appreciated that auxiliary handle 22 can be oriented so that it is generally perpendicular to handle 12.

Turning to FIG. 1, auxiliary handle 22 aids in the further support of retractor 10 by providing the operator an additional surface for gripping retractor 10. Auxiliary handle 22 preferably has a generally cylindrical shape with a larger medial diameter and smaller lateral diameters. This shape provides for comfortable gripping of handle 22. Although handle 22 is shown as generally cylindrical, handle 12 may be any shape, preferably a shape that conforms ergonomically and comfortably with an operator's fingers and hands. For example, handle 12 may be rectangular, cylindrical, octagonal, or hexagonal. Preferably located at a lateral end of auxiliary handle 22, threaded shaft 20 may be integral with auxiliary handle 22 or may be coupled to auxiliary handle 22. Alternative to threaded engagement, other methods of coupling auxiliary handle 22 to handle 12 have been contemplated. For example, handle 22 may be coupled to handle 12 via an interference fit or similar coupling.

Figure 3:
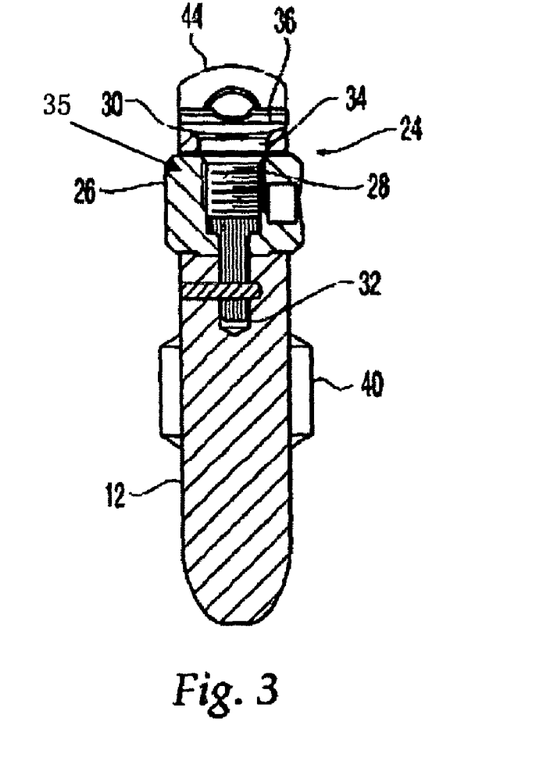
FIG. 3 is a cross-sectional view of a portion of the handle of FIG. 2 taken along line 3-3.

Located near proximal end 14 of handle 12 is a coupling mechanism 24 designed to secure interchangeable retractor blades to handle 12. As shown in FIG. 3, in an exemplary embodiment, coupling 24 comprises a knob 26 having an axial bore 28. Knob 26 is preferably rotatably coupled to handle 12 via axle 32. In an exemplary embodiment, axial bore 28 extends from approximately the center of knob 26 to the upper surface of knob 26 where it axially aligns with opening 34 in handle 12. Opening 34 extends from the cavity portion 35 of handle 12 where knob 26 is disposed to an upper surface 36 on handle 12. Axial bore 28 is preferably threaded. Preferably, knob 26 may be knurled or have some other form of texturing on its outside surface to enhance grip. In an exemplary embodiment, a shoulder 30 may also be included on handle 12 to aid in the coupling of an interchangeable retractor blade to handle 12.

Figure 5:
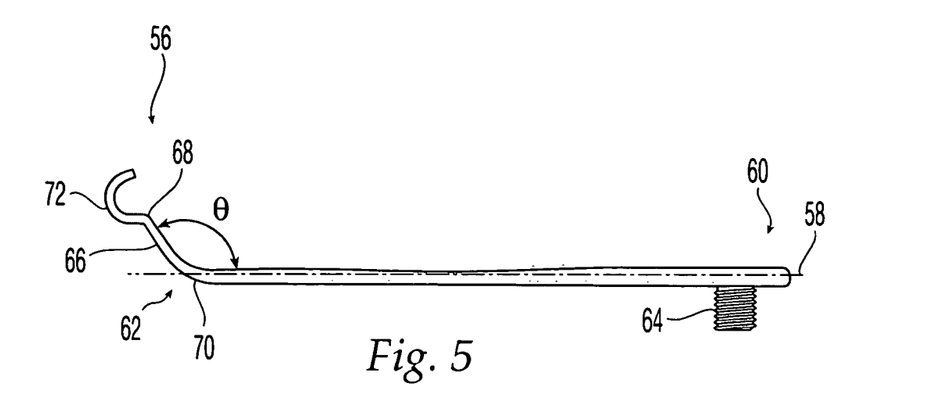
FIG. 5 is a side view of a first embodiment of an interchangeable retractor blade according to the present invention.
Figure 6:
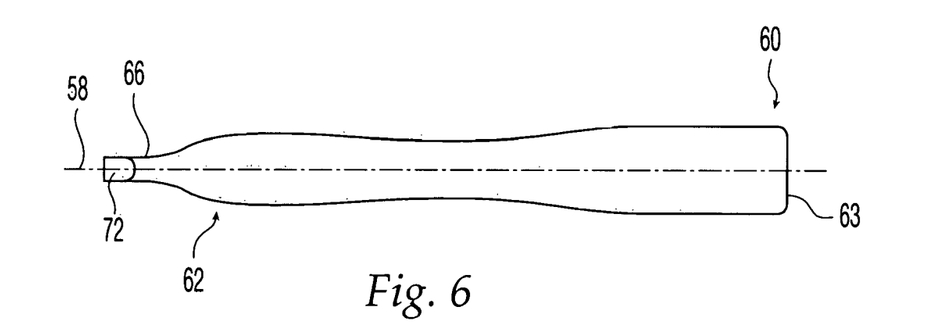
FIG. 6 is a top view of the interchangeable retractor blade of FIG. 5.

Referring to FIGS. 5 and 6, an exemplary interchangeable retractor blade 56 is shown. In an exemplary embodiment, the length of blade 56 may range from about 75 mm to about 150 mm and, preferably, range from about 95 mm to about 125 mm and the width of blade 56 may range from about 8 mm to about 25 mm and, preferably, range from about 10 mm to about 20 mm.

Blade 56 has a longitudinal axis 58, a proximal end 60, and a distal end 62. Located near proximal end 60, on the underside of blade 56, is a shaft 64. Shaft 64 is preferably threaded and is designed to engage axial bore 28 of knob 26 via opening 34 in upper surface 36 of handle 12. In an exemplary embodiment, the back end 63 of blade 56 may be straight to abut shoulder 30. In another exemplary embodiment, blade 56 may include a notch 65 (shown in FIG. 7) for engagement with a protrusion located on handle 12, as discussed earlier.

The back end 63 cooperates with shoulder 30 to position blade 56 on handle 12. The back end 63 of blade 12 and shoulder 30 on handle 12 may also cooperate to prevent blade 56 from rotating or pivoting on handle 12. Notch 65 on blade 56 and the protrusion on handle 12 also cooperate to position blade 56 on handle 12, and may also prevent blade 56 from rotating or pivoting on handle 12.

The proximal end 60 of blade 56 extends generally perpendicular to proximal end 14 of primary handle 12. The auxiliary handle 22 is preferably arranged so that it extends along an axis 23 that is approximately parallel to the longitudinal axis 58 of blade 56.

Referring to FIGS. 1 and 2, in an exemplary embodiment, located near proximal end 14 of handle 12 is another coupling mechanism 38 designed to secure a secondary surgical instrument, such as a light pipe or endoscope-type instrument, to handle 12. Coupling mechanism 38 and coupling mechanism 24 preferably operate independently of each other. Accordingly, coupling mechanism 38 may be used with a secondary surgical instrument without using coupling mechanism 24 and coupling mechanism 24 may be used with an interchangeable retractor blade without using coupling mechanism 38.

Figure 4:
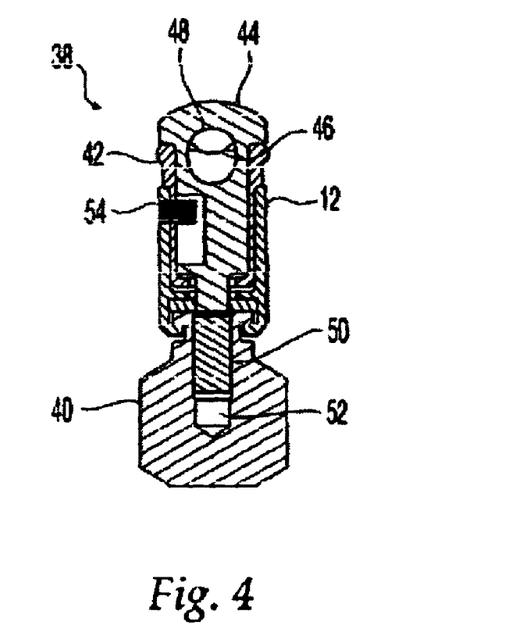
FIG. 4 is a cross-sectional view of a portion of the handle of FIG. 2 taken along line 4-4.

As shown in FIG. 4, in an exemplary embodiment, coupling mechanism 38 extends distally beyond the back end 63 of retractor blade 56. Coupling mechanism 38 comprises knob 40, an inner sleeve 42, and a clamping member 44. Knob 40 includes an axial bore 50 which preferably is threaded and extends from approximately the center of knob 40 to the upper surface of knob 40. Preferably, knob 40 may be knurled or have some other form of texturing on its outside surface to enhance grip. Inner sleeve 42 preferably surrounds a portion of clamping member 44 and has an upper surface 46 which is designed to operatively interface with clamping member 44 to lock a secondary surgical instrument in place, as discussed below. Clamping member 44 preferably includes a through-hole 48 located near its upper end for receiving a secondary surgical instrument and a shaft 52 extending downwardly from its lower end. Shaft 52 is preferably threaded and threadably engages axial bore 50 in knob 40.

As can be seen in FIGS. 1 and 4, handle 12 surrounds a portion of knob 40 and a portion of inner sleeve 42, which, in turn, surrounds a portion of clamping member 44. Preferably, sleeve 42 and clamping member 44 can rotate with respect to handle 12, but remain coupled to handle 12. In an exemplary embodiment sleeve 42, and clamping member 44 remain coupled to handle 12 via a pin 54, however, other methods of coupling may be used, such as, for example, snap-fitting. In another exemplary embodiment, handle 12 surrounds a portion of knob 40, a portion of inner sleeve 42, and a portion of clamping member 44, however, handle 12 surrounds these elements via an elongated opening. The elongated opening allows rotation of knob 40, sleeve 42 and clamping member 44 with respect to handle 12 and allows translation of knob 40, sleeve 42 and clamping member 44 with respect to handle 12.

As mentioned earlier, coupling mechanism 38 is designed to secure a secondary surgical instrument, such as a light pipe or endoscope-type instrument, to handle 12. In an exemplary manner of use, the operator of the retractor selects the desired surgical instrument and the instrument is introduced into through-hole 48 in clamping member 44 in a direction generally transverse to the longitudinal axis of handle 12. Clamping member 44 may be rotated to adjust the orientation of the instrument. In the other exemplary embodiment, clamping member 44 may be rotated or translated to further adjust the orientation of the instrument. Once the desired orientation of the instrument is achieved, knob 40 is rotated causing the threads in axial bore 52 to engage the threads on threaded shaft 52 of clamping member 44 to advance the threaded shaft 50 of clamping member 44 into axial bore 50. As threaded shaft 52 advances into axial bore 50, clamping member 44 moves downwardly with respect to inner sleeve 42. Since the surgical instrument passes through through-hole 48, as clamping member 44 moves downwardly with respect to inner sleeve 42, the surgical instrument becomes locked between the upper surface of through-hole 48 and upper surface 46 of inner sleeve 42. Further rotation of knob 40 results in the locking of inner sleeve 42 and clamping member 44 with respect to handle 12 since clamping member 44 moves downwardly with inner sleeve 42 until clamping member 44 abuts inner sleeve 42 which in turn abuts handle 12.

Retractor blade 56 may be configured in many different sizes and shapes. In a first exemplary embodiment shown in FIGS. 5 and 6, blade 56 has a first curved portion 66 having a distal end 68 and a proximal end 70 located at the distal end 62 of blade 56. Curved portion 66 preferably extends at an angle $\theta$ from longitudinal axis 58. In an exemplary embodiment, $\theta$ is between about 90° and about 150° and, preferably, is between about 110° and about 125°. Located near distal end 68 of curved portion 66 is a second curved portion 72. In an exemplary embodiment, second curved portion 72 has a generally hook-like shape that is semi-circular in shape with a radius of between about 1.5 mm to about 4 mm. Although shown as having a hook-shape, other shapes for curved portion 68 have also been contemplated, including, for example a truncated "C"-shape, and a "L" shape.

Blade 56 is preferably generally straight along longitudinal axis 58 from proximal end 60 to near distal end 62. As can best be seen in FIG. 8, in an exemplary embodiment, blade 56 may have a slight transverse concavity, for aiding in retraction, along its longitudinal length. The radius of the concavity of blade 56 preferably ranges from about 10 mm to about 20 mm radius. Further, in an exemplary embodiment, the width of blade 56 may vary along the longitudinal length of blade 56.

Figure 7:
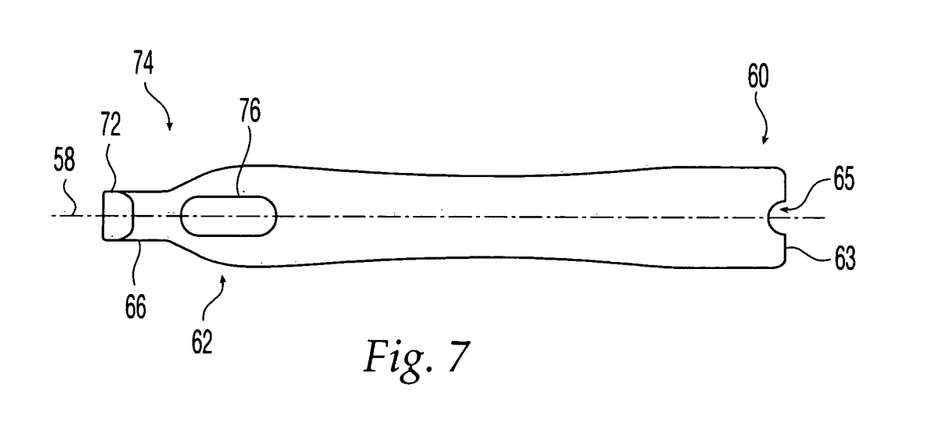
FIG. 7 is a top view of a second embodiment of an interchangeable retractor blade according to the present invention.

Referring to FIG. 7, an alternate exemplary embodiment of an interchangeable retractor blade 74 is shown. In general, most of the structure of blade 74 is similar or comparable to the structure of blade 56. Accordingly, the equivalent structures of blade 74 have been numbered the same as blade 56 and discussion of the similar components and features is not believed necessary. In this exemplary embodiment, an aperture 76 which extends through blade 74 from the upper surface to the lower surface is included near distal end 62 of blade 74. Aperture 76 preferably is configured and dimensioned to allow an operator to view or access subject matter located behind blade 74.

Figure 8:
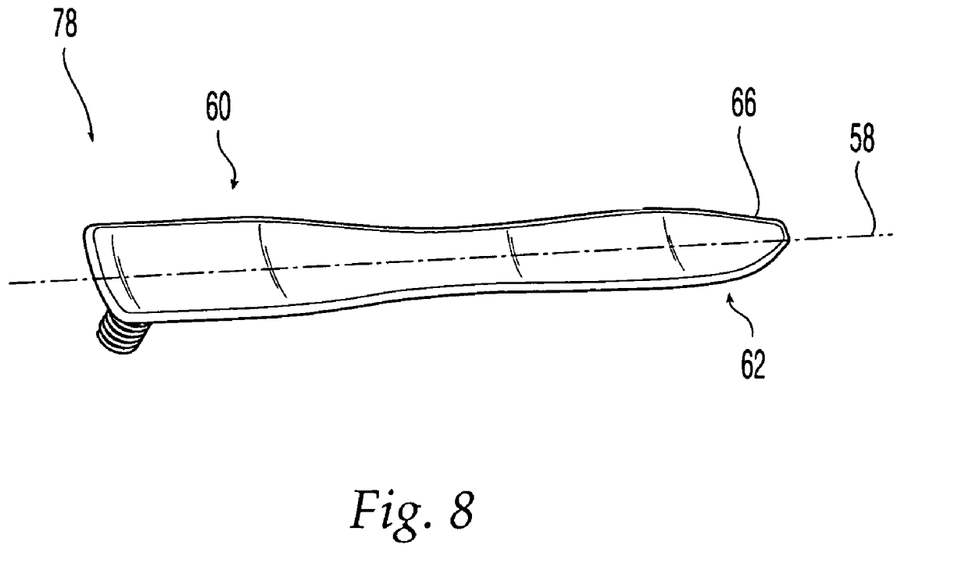
FIG. 8 is a perspective view of a third embodiment of an interchangeable retractor blade according to the present invention.

Turning now to FIG. 8, another exemplary embodiment of an interchangeable blade 78 is shown. In general, most of the structure of blade 78 is similar or comparable to the structure of blade 56. Accordingly, the equivalent structures of blade 78 have been numbered the same as blade 56 and discussion of the similar components and features is not believed necessary. In this particular embodiment, at distal end 62 of blade 78, instead of having first and second curved portions 66 and 72, blade 78 only has a first curved portion 66.

Referring back to FIGS. 1-3, as mentioned earlier, coupling mechanism 24 is designed to secure interchangeable retractor blade 56, 74, 78 to handle 12. In an exemplary manner of use, the operator of the retractor 10 selects a desired interchangeable retractor blade 56, 74, 78. The shaft 64 of the selected retractor blade 56, 74, 78 is introduced to axial bore 28 through opening 34 located on the upper surface 36 of handle 12. Knob 28 is rotated, via its edges, which extend radially outwardly from the sides of handle 12, causing the threads in axial bore 28 to engage the threads on the threaded shaft of retractor blade 56, 74, 78, to advance the threaded shaft of retractor blade 56, 74, 78 into axial bore 28. Preferably, knob 28 is rotated until a lower surface of the retractor blade 56, 74, 78 is flush with upper surface 36 of handle 12. In an exemplary embodiment, shoulder 30, located on upper surface 36 of handle 12, serves to abut the end of the retractor blade 56, 74, 78 preventing the blade from rotating with respect to handle 12 once it is coupled to handle 12. In another exemplary embodiment, shoulder 30 may have a protrusion (not shown) designed to engage a notch located in the retractor blade 56, 74, 78.

Although, in an exemplary embodiment, retractor blade 56, 74, 78 is threadably engaged to handle 12, other methods of coupling are contemplated. For example, retractor blade 56 can be coupled to handle 12 via an interference fit or a snap-fit.

Retractor blades 56, 74, 78 may be used in a variety of surgical procedures. One exemplary use of retractor 10 with retractor blade 56 is a maxillofacial procedure involving the mandible. Blade 56, in an exemplary embodiment, may include second curved portion 68 which is shaped to engage the ramus and condylar regions of the lower mandible.

As discussed earlier, in an exemplary embodiment, coupling mechanism 24 and coupling mechanism 38 are independently operable. Thus, primary handle 12 may include coupling mechanism 24, but not coupling mechanism 38. However, in an exemplary use, both coupling mechanisms may be used. Accordingly, in an exemplary use, an operator will use coupling mechanism 24 to couple retractor blade 56, 74, 78 to handle 12 and will use coupling mechanism 38 to couple a secondary surgical instrument to handle 12. Coupling mechanisms 24, 38 are configured and designed on primary handle 12 to permit the retractor blade and the secondary surgical instrument, i.e. a light cable or endoscope-type instrument, to interact in a manner such that the retractor blade and the secondary surgical instruments can perform their respective functions while avoiding interference with each other and the surgical procedure. In an exemplary manner of use, an operator selects the desired retractor blade 56, 74, 78 and couples blade 56, 74, 78 to handle 12 via coupling mechanism 24. The operator then selects the desired secondary surgical instrument, such as an endoscope, and couples the endoscope to handle 12 via coupling mechanism 38. Coupling mechanism 38 allows the orientation of the secondary surgical instrument to be adjusted. Accordingly, the operator will adjust the secondary surgical instrument to the desired orientation before locking it in place via coupling mechanism 38. In an exemplary use, retractor blade 56, 74, 78 will be situated generally parallel to the secondary surgical instrument, thereby preventing interference between the retractor blade and the secondary surgical instrument and avoiding interference with the surgical procedure.

The interchangeable retractor blades and handle may be packaged and sold as a kit which may include one or more retractor blades, one or more primary handles 12, one or more auxiliary handles 22, and potentially other accessories.

While various descriptions of the present invention are described above, it should be understood that the various features can be used singly or in combination thereof. Therefore, this invention is not to be limited to the specific preferred embodiments depicted herein. Further, it should be understood that variations and modifications within the spirit and scope of the invention may occur to those skilled in the art to which the invention pertains. For example, the interchangeable blades of the surgical retractor disclosed herein may not include any curvature at the distal portion thereof, and thus be a straight blade. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for treating bone comprising:
   providing a surgical retractor comprising:
      a handle having a longitudinal axis, proximal and distal ends, and a longitudinally elongated outer surface for being held by an operator, wherein the handle defines an enclosed perimeter of an opening;
      a first coupling mechanism coupled to the proximal end of the handle, wherein the first coupling mechanism comprises a knob having a threaded axial bore, wherein the knob is disposed within the opening and the knob is rotatable in the opening about the longitudinal axis of the handle; and
      a blade member having a proximal end and a distal end, and a threaded coupling element configured and dimensioned to be received in the threaded axial bore of the knob;
      a second coupling mechanism disposed on a backside of the handle proximate the proximal end of the handle;
   attaching an endoscope to the second coupling mechanism and positioning the endoscope with respect to the blade member for viewing a surgical site;
   making an incision in soft tissue and elevating the soft tissue fascia off a bone segment proximate the surgical site;
   passing a portion of the blade member through the incision;
   retracting the fascia off the bone segment with the blade member to form a cavity;
   circumventing at least in part a bone segment with a portion of the blade member;
   stabilizing the blade member on the bone segment;
   viewing the bone segment through the endoscope; and
   performing a surgical procedure proximate the bone segment.

2. The method of claim 1, further comprising securing the endoscope with respect to the blade member.

3. The method of claim 1, wherein performing the surgical procedure comprises passing an orthopedic implant through the cavity.

4. The method of claim 1, further comprising performing a part of the surgical procedure through an aperture of the blade member.

5. The method of claim 4, wherein performing the surgical procedure comprises passing a surgical tool through an aperture of the blade member.

6. The method of claim 5, wherein the tool comprises at least one of the group consisting of a drill, a burr, a syringe and a cannula.

7. The method of claim 4, wherein performing the surgical procedure comprises passing an orthopedic implant through the aperture.

8. The method of claim 7, wherein the implant comprises at least one of the group consisting of a bone fastener, a screw and a bone void filler material.

9. The method of claim 1, wherein performing the surgical procedure comprises securing an orthopedic implant to the bone segment.

10. The method of claim 9, wherein performing the surgical procedure comprises fixating a fracture proximate the bone segment.

11. The method of claim 10, wherein the bone segment comprises a condylar neck.

12. The method of claim 9, wherein performing the surgical procedure comprises performing an orthognathic procedure.

13. The method of claim 9, wherein performing the surgical procedure comprises a condylar grafting procedure.

14. The method of claim 13, wherein the bone segment comprises a ramus.

15. The method of claim 13, wherein the bone segment comprises a condylar neck.

16. The method of claim 1, wherein the blade member becomes detached from the handle when the coupling element is not received in the bore of the knob.

17. The method of claim 1, wherein the retractor further comprises a second coupling mechanism located on the handle for coupling the endoscope to the handle.

18. A surgical retractor comprising:
- a handle elongate along a longitudinal axis, the handle having a proximal end, a distal end, and an opening;
- a first coupling mechanism coupled to the proximal end of the handle, wherein the first coupling mechanism comprises a knob having a bore, wherein the knob is rotatable about the longitudinal axis;
- a second coupling mechanism disposed on a backside of the handle proximate the proximal end of the handle, the second coupling mechanism having a through-hole and at least a portion which is axially moveable within the opening of the handle, wherein the through-hole of the second coupling mechanism is sized and configured to receive a surgical instrument; and
- a blade member having a proximal end, a distal end, and a coupling element disposed proximate the proximal end of the blade member, wherein the coupling element is configured and dimensioned to be received in the bore of the knob, such that rotation of the knob in a first direction causes the coupling element to advance into the bore of the knob;
- wherein the coupling element of the blade member is configured and dimensioned to connect with the first coupling mechanism regardless of whether the surgical instrument is received in the through-hole of the second coupling mechanism, and the surgical instrument can be received in the through-hole of the second coupling mechanism regardless of whether the blade member is connected with the first coupling mechanism.

19. The retractor of claim 18, wherein the surgical instrument is an endoscope.

20. The retractor of claim 18, wherein the second coupling mechanism comprises a clamping member telescopically received within the handle.

21. The retractor of claim 20, wherein the clamping member is not in contact with the handle.

22. The retractor of claim 21, wherein the clamping member contacts a second member.

23. The retractor of claim 22, wherein the second member contacts the handle.

24. The retractor of claim 22, wherein the clamping member and the second member are operatively associated with each other to fix the surgical instrument with respect to the handle.

25. The retractor of claim 24, wherein the clamping member comprises a surface that defines a portion of the through-hole, the surface being adapted to receive a portion of the surgical instrument, and also adapted to clamp at least a portion of the surgical instrument to the second member.

26. A surgical retractor, comprising:
- a handle elongate along a longitudinal axis, proximal and distal ends, and a longitudinally elongate outer surface for being held by an operator;
- a first coupling mechanism coupled to the proximal end of the handle, wherein the first coupling mechanism comprises a knob having a bore, wherein at least a portion of the knob is disposed within the handle, and wherein the knob is rotatable about the longitudinal axis of the handle; and
- a blade member external to the handle, the blade member having a proximal end and a distal end, and
- (i) a coupling element extending from the proximal end in a direction angularly offset with respect to the blade member, wherein the coupling element is configured and dimensioned to be received in the bore of the knob such that the blade member extends in a direction that is angularly offset with respect to the longitudinal axis of the handle, and (ii) rotation of the knob in a first direction causes the coupling element to advance into the bore of the knob.

27. The retractor of claim 26, further comprising a second coupling mechanism located on the handle for coupling a second surgical instrument to the handle.

28. The retractor of claim 26, wherein the coupling element extends substantially perpendicular with respect to the blade member, and the blade member extends substantially perpendicular with respect to the longitudinal axis of the handle when the coupling element is received in the bore of the knob.

* * * * *